(12) United States Patent
Kumar et al.

(10) Patent No.: US 7,109,316 B2
(45) Date of Patent: Sep. 19, 2006

(54) OLIGONUCLEOTIDE TAGGED NUCLEOSIDE TRIPHOSPHATES (OTNTPS) FOR GENETIC ANALYSIS

(75) Inventors: Shiv Kumar, Belle Mead, NJ (US);
Anup Sood, Flemington, NJ (US);
Sudhakar Rao, Belle Mead, NJ (US);
John Nelson, Hillsborough, NJ (US)

(73) Assignee: CE Healthcare Bio-Sciences Corp., Piscataway, NJ (US)

( * ) Notice: Subject to any disclaimer, the term of this patent is extended or adjusted under 35 U.S.C. 154(b) by 451 days.

(21) Appl. No.: 10/226,734

(22) Filed: Aug. 23, 2002

(65) Prior Publication Data
US 2004/0038215 A1 Feb. 26, 2004

(51) Int. Cl.
C07H 21/02 (2006.01)
C07H 21/04 (2006.01)
C07H 19/04 (2006.01)
C12Q 1/68 (2006.01)

(52) U.S. Cl. .................. 536/23.1; 536/25.3; 536/26.6; 435/6

(58) Field of Classification Search .................. 435/6; 536/23.1, 25.3, 26.6
See application file for complete search history.

(56) References Cited

U.S. PATENT DOCUMENTS 5,863,727 A  1/1999  Lee et al. .................. 435/6
6,448,407 B1 * 9/2002  Lee et al. .................. 546/283.1
6,790,945 B1 * 9/2004  Lukhtanov et al. ........ 536/23.1

OTHER PUBLICATIONS

Hausch et al. Tetrahedron Letters 39 (1998) 6157-6158.*
Rosenblum, B. B., et al. "New dye-labeled terminators for improved DNA sequencing patterns" Nucleic Acids Research, 1997, vol. 25, No. 22 Oxford University Press pp. 4500-4504.

* cited by examiner

*Primary Examiner*—Jezia Riley
(74) *Attorney, Agent, or Firm*—Yonggang Ji (57) ABSTRACT

Oligonucleotide tagged nucleoside triphosphates, OTNTPs, which are substrates for polymerases and or terminal nucleotidyl transferases are provided as well as methods of making these OTNTPs. Further provided are OTNTPs with fluorescent dyes including energy transfer dyes, attached to the oligonucleotide chain, OTNTPs with unnatural bases incorporated in the oligonucleotide sequence and methods for incorporating these OTNTPs in DNA or RNA. Also provided are methods for using the oligonucleotides on OTNTPs for amplifying the oligo sequence on the OTNTP using an amplification method described above. Further provided are reactive bifunctional amidites, methods of making these compounds and methods for detecting single nucleotide polymorphisms using the above OTNTPs. Methods for detecting differential gene expression using the OTNTPs and methods of separating specifically modified DNA or RNA using the OTNTPs are also provided.

3 Claims, 10 Drawing Sheets

Where R and R' are independently selected from H, OH, OCH$_2$CH$_3$, N$_3$, SH, NCO, NCS, SCN, NH$_2$, F, Cl, NR"R"'; where R" & R"' are independently selected from H or small chain alkyl
X = O, S, CH$_2$ or BH$_3$
N is a ribose, deoxyribose, a ribonucleoside or a deoxyribonucleoside connected to each other by phosphodiester or any other linkage, and one or more N's may be labeled
n is between 2-100
linker is a linear or branched alkynyl, alkenyl, alkyl, alkylaryl, aryl, arylalkyl containing one or more heteroatoms and is attached to the base Structures of prefered OTNTPs Where R and R' are independently selected from H, OH, OCH$_3$, CH$_3$, N$_3$, SH, NCO, NCS, SCN, NH$_2$, F, Cl, NR"R'"; where R" & R'" are independently selected from H or small chain alkyl
X = O, S, CH$_3$ or BH$_3$
N is a ribose, deoxyribose, a ribonucleoside or a deoxyribonucleoside connected to each other by phosphodiester or any other linkage, and one or more N's may be labeled
n is between 2-100
linker is a linear or branched alkynyl, alkenyl, alkyl, alkylaryl, aryl, arylalkyl containing one or more heteroatoms and is attached to the base Figure 1: Structures of prefered OTNTPs Figure 2: Synthesis of a nucleoside phosphoramidite for making OTNTPs Figure 3: Synthesis of a bifunctional linker amidite Figure 4: Synthesis of a fluorescein labeled OTNTP for direct detection after incorporation Figure 5: Synthesis of a fluorescein labeled OTNTP with a $T_6$ sequence as oligonucleotide tag on a solid support Figure 6: Synthesis of Energy-Transfer Oligonucleotide tagged ddNTP Figure 7: Sequencing of M13 template using FAM-linker-ddUTP and its comparisor with correct sequence obtained with a commercial energy transfer terminator.

Figure 8: Sequencing of M13 template using FAM-LpLp-linker-ddATP

Figure 9: Sequencing of M13 template using FAM-TTTTTT-linker-ddUTP

Figure 10: Sequencing of M13 template using FAM LpLpLpLpLpLpLpLpT*-linker-ddUTP

OLIGONUCLEOTIDE TAGGED NUCLEOSIDE TRIPHOSPHATES (OTNTPS) FOR GENETIC ANALYSIS

BACKGROUND OF THE INVENTION

1. Field of the Invention

A new class of nucleoside triphosphates that contain an oligonucleotide of random or defined sequence attached to the base and are substrates for polymerases and terminal nucleotidyl transferases is described. The present invention further describes new reactive bifunctional linker amidites that can be used for the synthesis of the new class of nucleoside triphosphates. Furthermore, this invention describes the methods of making these amidites and triphosphates as well as methods of using these nucleoside triphosphates for genetic analysis.

2. Description of Related Art

Sequencing of human and other genomes has provided an array of opportunities in genetic analysis for the purposes of improving human and animal health, food and water safety, forensics, crop protection, etc., to name a few. Genotyping of individuals and populations will allow the feasibility of tailored therapies suited to individuals or patient groups. Identifying metabolic differences in patient groups based upon genetic polymorphism will provide improved dosing regimens, enhancing drug efficacy and safety. Understanding the genetic basis of disease will provide new drug targets, decrease drug development costs, increase chances of success in clinical development and overall maximize commercial potential. Similarly understanding the genetic basis of disease in animal and plants will help engineer disease resistant animals & crops as well as enhance desirable characteristics.

In addition to looking at genetic differences, differential expression analysis of various genes is very important. In many cases, genes relevant for a particular disease may be expressed in very low copy number. Identifying and quantitating these low copy genes requires very high sensitivity assays and will generally require some type of amplification. A number of amplification methods, such as Ligase Chain reaction (LCR), Polymerase Chain Reaction (PCR), Strand Displacement Amplification (SDA), Self-Sustained Sequence Replication (3SR) also known as Nucleic Acid Sequence Based Amplification (NASBA), QB Replicase amplification and Rolling Circle Amplification (RCA), have been developed (J. Virological Methods, 1991, 35, 117–126). A generally accepted definition of amplification and the term amplification, as referred to herein, includes making copies of an original sequence and/or a complementary sequence. Most of these methods have high background as sequences being amplified although unique are not substantially different from sequences in other regions of the genome. Therefore a method that adds a highly unique sequence to the target for amplification and/or detection can provide higher sensitivity and hence is desirable.

Fluorescence detection methods are widely used for detection of DNA or RNA due to their high sensitivity and lower toxicity compared to radiolabels. For a number of applications and especially for multiplexing, several fluorophores with distinguishable characteristics are required. For example, in sequencing, 4 different fluorescent dyes are used to distinguish different nucleoside bases. An ideal set of dyes will absorb at the same wavelength, but emit at readily differentiable wavelengths at similar intensities. Unfortunately, it is extremely difficult to find such a set of dyes. In order to circumvent this problem, fluorescence energy transfer systems have been designed, where a single dye is used to absorb energy which then acts as a donor to transfer energy to a set of acceptor dyes emitting at different wavelengths. For genetic analysis, including sequencing, energy transfer systems have been used in two ways; primers labeled with energy transfer dyes (Ju. J. et. al., Proc. Natl. Acad. Sci. USA 1995, 92, 4347–4351; Hung S. C. et. al., Anal. Biochem. 1996, 243, 15–27 and Hung S. C. et. al., Anal. Biochem. 1997, 252, 78–88) and nucleoside triphosphates labeled with energy transfer dyes (Rosenblum B. B. et. al., Nucleic Acids Res., 1997, 25, 4500–4504; Lee L. G. et. al., Nucleic Acids Res. 1997, 25, 2816–2822; Nampalli, S. et. al. Tet. Lett. 2000, 41, 8867–8871; Lee L. G. et. al., 1999, U.S. Pat. No. 5,863,727; Kumar S, et. al. 2000, PCT WO 00/13026; Rao, T. S. et. al., Nucleosides, Nucleotides & Nucleic Acids, 2001, 20, 673–676). The latter is desirable as it is easier to separate labeled nucleoside triphosphates from labeled product than labeled product from labeled primer. In addition labeled primers also result in higher background as all extension products are labeled.

However, energy transfer between dyes attached to different bases on a primer has been found to be more efficient than when the dyes are attached to each other via other linkers. The reasons for this are not well understood, but it is possible that the right conformation with the linkers tried so far, has not been achieved or the DNA bases somehow facilitate the energy transfer. Therefore it is desirable to combine the desirable properties of both systems.

Accordingly, there is a need for high sensitivity, high specificity methods that are easily multiplexed. This concern is addressed in greater detail below.

SUMMARY OF THE INVENTION

The current invention provides methods that will reduce background and hence increase sensitivity of many of the amplification techniques described above. The current invention provides oligonucleotide tagged nucleoside triphosphates, OTNTPs, which are substrates for polymerases and or terminal nucleotidyl transferases as well as methods of making these OTNTPs. The current invention further provides OTNTPs with fluorescent dyes including energy transfer dyes, attached to the oligonucleotide chain, OTNTPs with unnatural bases incorporated in the oligonucleotide sequence and methods for incorporating these OTNTPs in DNA or RNA Additionally, the current invention provides methods for using the oligonucleotide on OTNTPs for amplifying the oligo sequence on the OTNTP using an amplification method described above. The current invention provides reactive bifunctional amidites, methods of making these compounds and methods for detecting single nucleotide polymorphism using OTNTPs of the current invention. Further, the current invention provides methods for detecting differential gene expression using OTNTPs of current invention. Finally, the current invention provides methods of separating specifically modified DNA or RNA using OTNTPs of the current invention.

Disclosed are compositions and methods of making reactive bi-functional amidites and OTNTPs as well as methods of incorporating these OTNTPs into DNA or RNA. These methods are useful for detecting genetic variations as well as differential gene expression. Due to target discrimination at two levels (target specific hybridization and primer extension) and ease of multiplexing due to energy transfer dyes, this method is suitable for genetic analysis requiring high sensitivity and specificity. Additional sensitivity can be achieved by incorporating unnatural bases in oligonucleotide sequence of OTNTPs that code for another unnatural base and not for any of the natural bases and/or by omitting one or more of the natural bases. One of the reasons for low sensitivity of many assays is the background generated by non-specific hybridization of probes to the target. This can be a major problem in assays where the signal is further amplified after hybridization. By incorporating unnatural bases or by omitting one or more of the natural bases in the oligonucleotide sequence of OTNTP's, it should be easier to control non-specific hybridization of probes or targets to this sequence, thereby reducing background and hence enhance sensitivity. A preferred embodiment of present invention consists of hybridizing a primer to a pre-amplified target, incorporating an OTNTP terminator of the present invention bearing a fluorescent donor and acceptor dye, separating the unincorporated OTNTPs from labeled primer and identifying the OTNTP incorporated. OTNTP terminators are OTNTP which after incorporation of the terminator do not support further primer extension.

Another preferred embodiment of this method consists of target specific hybridization of a primer, extension of the primer with OTNTPs, where each terminator representing a different base has a specific oligonucleotide sequence associated with that base, removing the unincorporated terminators, amplifying the incorporated OTNTP sequence using rolling circle amplification and detecting the amplified sequence using methods known in prior art. Yet another preferred embodiment of this invention consists of labeling cDNA using OTNTPs of the current invention. The above features of the invention will become more fully apparent when the following detailed description of the invention is read in conjunction with the accompanying drawings.

DETAILED DESCRIPTION OF THE INVENTION

The invention is based on the discovery that nucleoside triphosphates bearing an oligonucleotide on the base, are substrates for DNA polymerases. One skilled in the art would appreciate that after incorporation, the oligonucleotide sequence on the base can act as any other oligonucleotide sequence. Hence, it can be used as a template or a primer for further manipulations, such as amplification, or as a target for a labeled probe.

The predominant method used today to sequence DNA is the Sanger method (Proc. Natl. Acad. Sci. 1977, 74, 5463) which involves use of dideoxynucleoside triphosphates as DNA chain terminators. All high throughput-sequencing systems use this approach in combination with use of fluorescent dyes. The dyes may be attached to the terminator or be a part of the primer. The former approach is preferred as only the terminated fragments are labeled. As described earlier for multiplexing energy transfer fluorescent dyes are preferable over the use of single dyes.

Use of fluorescence resonance energy transfer primers has been described by Ju, J. et. al. (Proc. Natl. Acad. Sci. USA 1995, 92, 4347–4351). Primers were designed based on the concept in which fluorescein was attached to the 5'-end of the primer as a common donor and a rhodamine dye (R110, REG, TAMRA and ROX) was attached at an optimal distance using a modified T in the primer. Optimal distance was determined by measuring the emission of acceptor dye by varying the distance between the donor and acceptor dyes. This distance was found to be 10 bases for this combination of dyes. Optimal distances are expected to vary with combination of dyes used. Somewhat shorter or longer than optimal distances may also be acceptable as long as sufficient energy transfer suitable for detection does occur.

In another approach an abasic oligo bearing both donor and acceptor was synthesized and attached to the 5'-end of a primer using a disulfide linkage (Berti, L. et. al., Anal. Biochemistry, 2001, 292, 188–197). In both cases, however, the label was on the primer. It is well known in the art that use of labeled primers generally gives higher background than labeled terminators. It is therefore, an object of the current invention to provide DNA chain terminators with energy transfer dyes having high quantum yields. The current invention differs from the prior art in that the labeled oligonucleotide bearing both donor and acceptor are part of the terminator and the primer is only labeled when one of these OTNTPs is incorporated.

The OTNTP terminators of current invention that are labelled with energy transfer dyes also differ from the energy transfer terminators known in the prior art (Rosenblum B. B. et. al., Nucleic Acids Res., 1997, 25, 4500–4504; Lee L. G. et. al., Nucleic Acids Res. 1997, 25, 2816–2822; Nampalli, S. et. al. Tet. Lett. 2000, 41, 8867–8871; Lee L. G. et. al., 1999, U.S. Pat. No. 5,863,727; Kumar S, et. al. 2000, PCT WO 00/13026; Rao, T. S. et. al., Nucleosides, Nucleotides & Nucleic Acids, 2001, 20, 673–676) in that the two dyes (donor & acceptor dye) are not linked together but attached to different bases on the OTNTP oligo and allow for a better and easy control over distance between the two dyes. The OTNTP of current invention are represented by formula 1 as shown below.

Formula 1 wherein
R and R' independently represent H, OH, $OCH_3$, $CH_3$, $N_3$, SH, NCO, NCS, SCN $NH_2$, F, Cl or NR"R'",
   wherein R" and R'" independently represent H or a small chain alkyl, such as C1–C5 alkyl.

X represents O, S, $CH_3$ or $BH_3$;

Base represents uracil, cytosine, thymine, adenine, guanine, hypoxanthine, 2-aminopurine, 2,6-diaminopurine, xanthene, deazaadenine, deazaguanine or an analog thereof;

Linker represents a linear or branched alkynyl, alkenyl, alkyl, alkylaryl, aryl, or arylalkyl containing one or more heteroatoms selected from the groups consisting of N, O, S and P, and is attached to the base at the N4 or C5 position of pyrimidines or N6, C7 or C8 position of purines or other sites when modified bases are used;

N represents a ribose, deoxyribose, a natural or unnatural deoxyribonucleoside or a natural or unnatural ribonucleoside, optionally containing a detectable moiety;

n represents an integer from 2 to 100; and wherein each N is linked to at least one other N by phosphodiester, phosphorothioate, alkyl phosphonate, or other linkages.

The present invention describes methods of incorporating OTNTP's of current invention into DNA or RNA using DNA or RNA polymerizing enzymes. These methods include incubating a DNA or RNA sample with or without primer, in the presence of one or more OTNTP's of current invention and one or more of the DNA or RNA polymerizing enzymes. DNA polymerizing enzymes include DNA polymerases, reverse transcriptases and terminal deoxynucleotidyl transferases. RNA polymerizing enzymes include RNA polymerases, primases and terminal nucleotidyl transferases.

The present invention also describes methods of detecting a specific nucleotide sequence in a biological sample. The methods comprise the following steps:

1) hybridizing a sequence specific primer to the target molecule,
2) sequence specifically extending the primer using a set of OTNTPs of formula 1, and either
3a) detecting the incorporated base via detecting the label attached to OTNTP or using a labeled probe specific for the OTNTP sequence, or
3b) amplifying the OTNTP sequence using any one of the several known amplification methods and detecting the amplified product using methods known in the art
4) optionally quantifying the amount incorporated.

It should be noted that the oligonucleotide sequence of an OTNTP might also be used as an affinity tag to separate oligonucleotide/DNA sequences where this OTNTP has been incorporated. In this aspect of the invention, the oligonucleotide sequence of the OTNTP acts as an affinity tag. This affinity tag may be added sequence specifically using a polymerase and one of the OTNTP's. It can then be captured on to a solid support using a complementary oligonucleotide sequence (complementary to the sequence of the affinity tag) to isolate only the DNA or RNA incorporating a particular OTNTP. Once captured, the unbound material can be readily washed away and captured sequence may be eluted from the solid support by washing with a denaturing buffer.

Alternatively, it is possible to add this affinity tag to all DNA or RNA present in a sample using a terminal nucleotidyl transferase (deoxynucleotidyl or ribonucleotidyl) and an OTNTP with deoxyribo or ribose sugar. This could be useful for separating DNA or RNA from a mixture of DNA, RNA, protein and other components in the sample.

The length of oligonucleotide on the OTNTP can vary and the desired length is a function of application to which these OTNTPs are applied. For applications where sufficient sample is available and these OTNTPs are only used for distinguishing the base incorporated, a length of 2–15 nucleotides may be sufficient depending upon the energy transfer efficiency of the dyes used or the length of probe. If on the other hand the oligonucleotide tag is used as a primer, e.g. in RCA, a length of 6 or more nucleotides will be required. Preferably this length would be between 10–25 nucleotides. Finally, if the oligonucleotide on the terminator is used as a template, even longer lengths may be needed. An embodiment of the current invention provides OTNTPs of formula 1, wherein oligonucleotide represents a sequence of bases ranging in length from 2–100 bases and may or may not contain a label. A label is a moiety that can be detected by any of the methods used in prior art, including colored dyes, fluorescent compounds, mass tags, compounds that generate luminescence, radiolabels, electrochemical tags.

A preferred embodiment of current invention provides OTNTPs of structure 1a–h, (see FIG. 1) where each oligonucleotide is labeled with a unique fluorescent dye.

Another embodiment of current invention provides OTNTPs of structure 1a–h, wherein each oligonucleotide is modified by attachment of a donor dye, which is common to all four nucleotides and an acceptor dye, which is unique to each nucleotide. Furthermore, a distance appropriate for energy transfer separates these dyes. Most commonly used energy transfer pair is fluorescein/rhodamine, but other ET pairs Cy3/Cy5, Fluorescein/Cy5, Fluorescein/Cy5.5, etc. have also been successfully employed (U.S. Pat. No. 6,245,514 B1 and references cited therein) and are incorporated herein by reference.

Another embodiment of current invention provides OTNTPs of structure 1a–h, where the oligonucleotide sequence is comprised of abasic nucleotides labeled with a donor and acceptor dye wherein the donor dye is common to all OTNTPs while acceptor dye is different for each OTNTP. Furthermore, the donor and acceptor dyes are separated by a distance appropriate for energy transfer. It should be noted that the oligonucleotide sequence of the OTNTP in this embodiment could not be used as a template or primer for further amplification.

Another embodiment of the invention describes a method of genetic analysis comprising
   a) mixing a sample of DNA or RNA target with a sequence specific primer in an aqueous buffer;
   b) adding a polymerase, a set of four OTNTP terminators bearing unique oligonucleotide sequences to form a mixture;
   c) incubating this mixture at a temperature suitable for polymerase activity; and
   d) detecting the OTNTP incorporated by hybridization with a labeled probe.

The probe may be labeled with any detectable moiety that can be uniquely identified. Such detectable moieties include fluorescent dyes, colored or luminescent moieties, mass tags and electrochemical tags. Examples of these moieties are widely available in the chemical literature.

Another embodiment of the invention describes a method of genetic analysis comprising
   a) mixing a sample of DNA or RNA target with a sequence specific primer in an aqueous buffer;
   b) adding a polymerase, a set of four OTNTP terminators bearing a detectable label to form a mixture;

c) incubating this mixture at a temperature suitable for polymerase activity for a time sufficient to incorporate an OTNTP; and
d) detecting the OTNTP incorporated by detecting the label.

DNA or RNA targets include chemically modified DNA, which can still hybridize sequence specifically, e.g. bisulphite treated DNA. OTNTP terminators are OTNTPs with modified sugar, e.g. dideoxyribose, so that after incorporation of OTNTP, further elongation of primer is not feasible.

Another embodiment of the invention describes a method of genetic analysis comprising
 a) mixing a sample of DNA or RNA target with a sequence specific primer in an aqueous buffer;
 b) adding a polymerase, a set of four OTNTP terminators bearing OTNTP specific fluorescent dyes to form a mixture;
 c) incubating this mixture at a temperature suitable for polymerase activity for a time sufficient to incorporate an OTNTP; and
 d) detecting the OTNTP incorporated by detecting the dye incorporated.

A variety of fluorescent dyes are commercially available and include fluoresceins, rhodamines, cyanines, bodipy dyes, coumarins, to name a few. Any fluorescent dye that is stable under the incorporation conditions may be used.

Another embodiment of the invention describes a method of genetic analysis comprising
 1) mixing a sample of DNA or RNA target with a sequence specific primer in an aqueous buffer;
 2) adding a nucleic acid polymerase, a set of four OTNTP terminators bearing a donor and acceptor dye at a distance optimal for energy transfer each acceptor dye being specific to a particular base and emitting at a different wavelength than other acceptor dyes to form a mixture;
 3) incubating this mixture at a temperature suitable for polymerase activity for a time sufficient to incorporate an OTNTP; and
 4) detecting the OTNTP incorporated by exciting the donor dye and measuring the emission from the acceptor dye.

As described above, it is possible to use the oligonucleotide sequence of OTNTPs for amplification. This sequence can be chosen so that it is not only unique but also drastically different from any possible sequences that can be found naturally. This can be achieved by adding unnatural bases to the sequence that code for either themselves or other unnatural bases. Examples of these unnatural bases are cited in Lei Wang et. al. J. Am. Chem. Soc. 2000, 122, 5010–5011 and references therein and are incorporated herein by reference.

Another embodiment of current invention describes a method of genetic analysis by
 a) mixing a DNA or RNA target with a sequence specific primer in an aqueous buffer,
 b) adding a polymerase and a set of OTNTP terminators to form a mixture,
 c) incubating the sample at a temperature suitable for polymerase activity for time sufficient to incorporate an OTNTP,
 d) separating the extended primer from unincorporated OTNTPs,
 e) adding a set of 4 single stranded circular DNA each having a different sequence, complementary to one of the four oligonucleotide sequences of the OTNTPs,
 f) adding DNA polymerase suitable for RCA and other reagents (dNTPs, buffer, salts, etc.) required for RCA,
 g) performing RCA by incubating at appropriate temperature for a time sufficient for amplification, and
 h) detecting the signal by hybridizing the RCA product with sequence specific ampliflours or molecular beacons.

Amplifluors and molecular beacons are oligonucleotides bearing a fluorescent dye and a quencher dye. As such these oligonucleotides exist in a three-dimensional structure where the fluorescence of the fluorescent dye is completely or partially quenched. Upon hybridization to target (in this case amplified RCA product), the fluorescent dye and quencher are pulled apart and fluorescence is no longer quenched.

Figure 1:
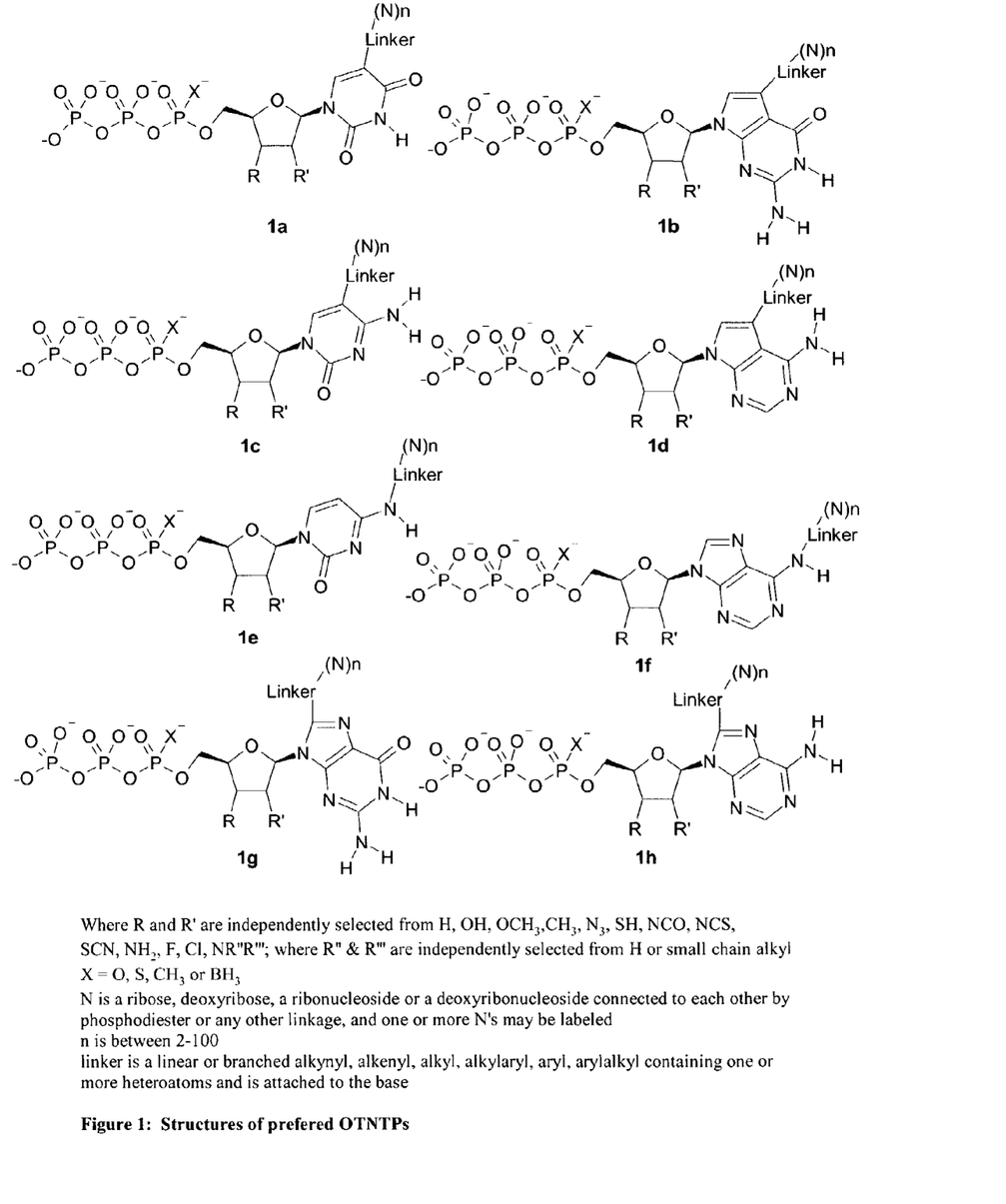
FIG. 1: Structures of preferred OTNTPs.

Another embodiment of current invention provides OTNTPs of the structures shown in 1a–h, of FIG. 1, where the oligonucleotide contains one or more unnatural bases.

In another type of homogenous assay, gamma labeled dNTPs may be used during amplification. Gamma labeled dNTPs used in this method are labeled with dyes that either fluoresce only after being released from dNTP and removal of phosphate groups or emit at a different wavelength as a free dye. Examples of these dyes include but are not limited to 7-hydroxy-acridin-2-one's, 7-hydroxy-coumarins, resorufin, etc. to name a few. In addition to fluorescent dyes, it is possible to use other chromogenic substrates that have measurably different properties in the free form from when they are attached to the gamma phosphate of dNTP. Some of the examples of chromogenic substrates useful in this invention are disclosed in U.S. Pat. Nos. 5,191,073; 5,208,326; 4,932,871; 5,183,743; 4,810,636 and 5,122,608, and are incorporated herein by reference. The dyes described here are for the purpose of providing examples and in no way should be considered to be limiting the scope of this invention.

Another embodiment of current invention describes a method of genetic analysis by
 a) mixing a DNA or RNA target with a sequence specific primer in an aqueous buffer,
 b) adding a polymerase and a set of OTNTPs to form a mixture,
 c) incubating the mixture at a temperature suitable for polymerase activity for a time sufficient to incorporate a terminator
 d) removing unincorporated terminators from the extended primer
 e) adding a set of 4 single stranded circular DNA each having a sequence different from others and in such a manner that the ratio of G,A,T and C for each sequence is substantially different from others, and at the same time part of the sequence being complementary to one of the four oligonucleotide sequences of the OTNTPs,
 f) adding a DNA polymerase suitable for RCA, a set of 4 gamma labeled dNTPs (as described above) and other reagents (buffer, salts, etc.) required for RCA and a phosphatase,
 g) performing RCA by incubating at appropriate temperature for a time sufficient for amplification or until all the nucleotides are consumed, and
 h) measuring the ratio of dyes released and hence identifying the sequence amplified.

The ratio of G,A,T,C in different circles has to be substantially different from each other so that the ratio of dyes released for amplification of one circle can be easily differentiated from the ratio of dyes released if a different circle was amplified. For example, if the ratio of dyes released from amplification of one circle is 1:1:1:1 and for a different circle it is 1:1:0.95:1, it may not be possible to differentiate between the two. If on the other hand these ratio are 1:1:0.5:1 vs 1:1:1:1.25, they should be readily differentiated.

Further, it is possible to come up with a fairly unique sequence using natural bases by totally omitting one or two of the bases in the sequence. It is further preferred that in the above mentioned embodiment, each of the circular template used for RCA and the oligonucleotide tags on OTNTPs consist of nucleotides representing only 3 of the four natural bases. The missing base in each circle and the complementary oligonucleotide tag is different from the missing bases in other circles and oligonucleotide tags. In this preferred embodiment, when each gamma labeled dNTP is labeled with a different dye, only three of the four dyes will be released and hence readily identify the sequence amplified.

As described earlier, a number of amplification methods have been developed for the amplification of target oligonucleotide and can be used in conjunction with current invention. For example, the oligonucleotide tag on the incorporated OTNTP may act as a primer or template in PCR, LCR or SDA, a primer in 3SR and RCA (as described above) or a target for amplification by Qβ Replicase.

Thus, another embodiment of current invention describes a method of genetic analysis by
 a) mixing a DNA or RNA target with a sequence specific primer in an aqueous buffer,
 b) adding a polymerase and a set of OTNTPs to form a mixture,
 c) incubating the mixture at a temperature suitable for polymerase activity for a time sufficient to incorporate a terminator,
 d) separating the unincorporated OTNTPs,
 e) amplifying the terminator oligonucleotide sequence using one of amplification method known in the art,
 f) identifying amplified sequence by one of the methods known in the art.

It should be noted that separation of unincorporated terminators may or may not be essential or may be carried out after amplification. For example if the original primer is attached to the surface, the oligonucleotide tag of the incorporated OTNTP will get anchored to the surface and hence any amplification of this tag may also remain anchored to the surface. So even if the unincorporated OTNTPs are not removed prior to amplification, they can be washed off in subsequent steps. It is also possible to detect this anchored product using internal reflectance fluorescence microscopy without having to separate the unanchored products.

Another embodiment of current invention describes a method of detecting differential gene expression by using the OTNTP's of the present invention. Monitoring expression of different genes in different tissues (different tissue types, same type of tissue at different stages of development or normal vs. diseased tissue) is of great importance in determining the role of various genes in development of different organs or diseases. Methods for detecting this differential expression generally involve following steps:
 a) separately amplifying the messages in two tissues by making multiple copies of labelled message using a labelled NTP or corresponding labelled cDNA using a labelled dNTP (a different label is used for each tissue sample)
 b) mixing the two amplified products
 c) separating the labelled messages or cDNA copies on a DNA chip by hybridization, and
 d) detecting the site and ratio of two labels on the chip.

While site determines the gene being expressed, the ratio indicates the amount of expression of that gene in different tissues. OTNTP's of the current invention can be used for this purpose. In this case an OTNTP with one oligo sequence is incorporated in messages of one tissue sample and an OTNTP with same base but a different oligo sequence is incorporated in the messages of other tissue sample. After mixing the samples and separating the messages on a chip, the site and amount of two oligo sequences of OTNTP's can be determined by any one of the methods described above. An advantage of using oligo tags vs other detectable moieties such as fluorescent dyes is that signal can be further amplified by amplifying the oligo tag sequence.

In order to make these OTNTPs, a variety of methods are available that can be classified into two categories, solid phase methods and mixed solid/solution phase. In solid phase methods, the complete OTNTP is synthesized on a solid support and after cleavage and deprotection is purified for use in genetic analysis. In mixed solid/solution phase methods, the oligonucleotide is synthesized on the solid support and then attached to the nucleoside triphosphate in solution. Thus, another embodiment of this invention provides a method of making these OTNTPs on solid support (FIG. 5) comprising following steps:
 a) Synthesizing the desired oligonucleotide sequence on a solid support using routine automated DNA synthesis using fast deprotecting protecting groups on DNA bases,
 b) Adding a reactive group to the oligonucleotide using a reactive bifunctional amidite of the present invention described below,
 c) Incubating the solid support with a functionalized nucleoside triphosphate where the functional group is capable of reacting with the second reactive functional group of the bifunctional amidite,
 d) Cleaving the oligonucleotide from support and deprotecting the bases.

Figure 5:
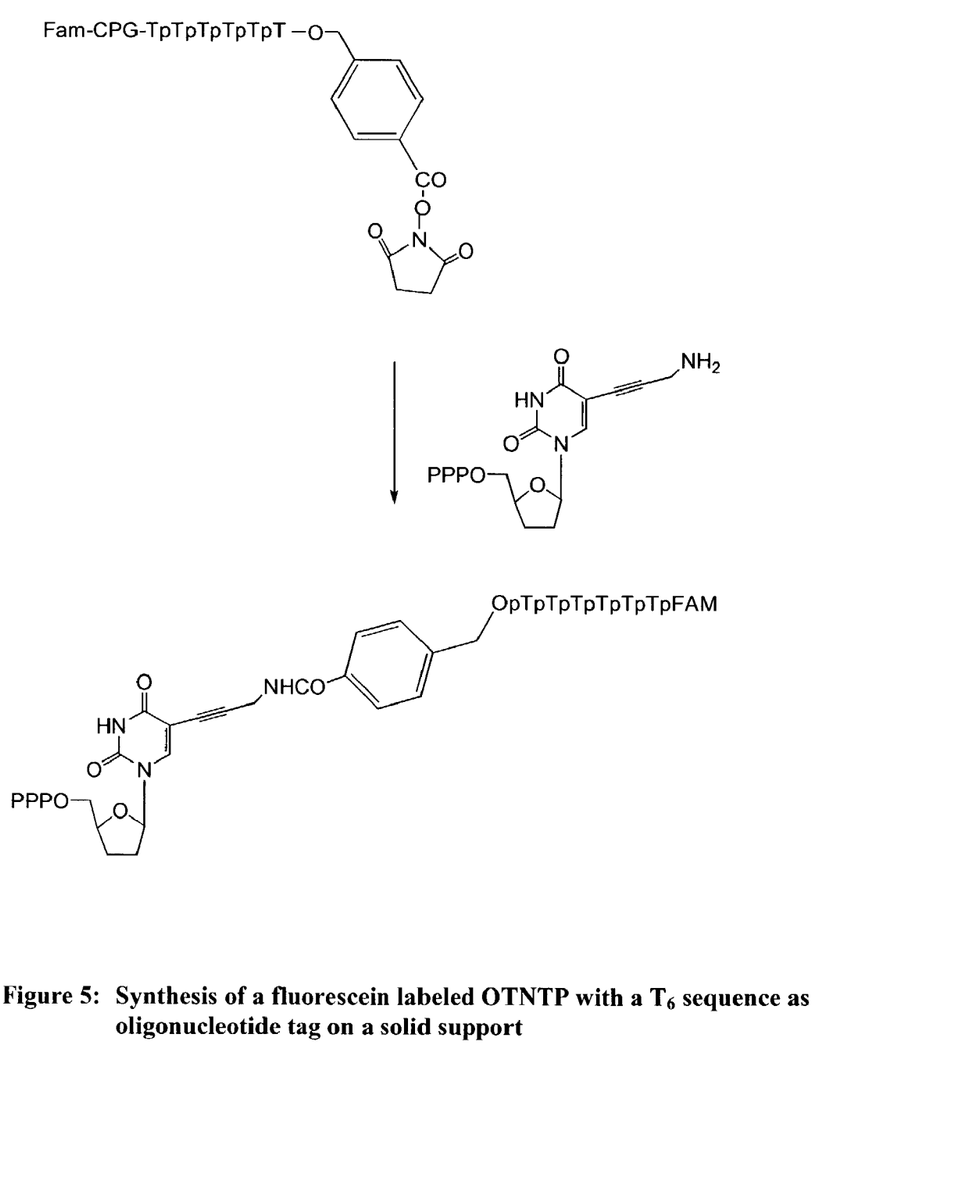
FIG. 5: Synthesis of a fluorescein labeled OTNTP with a $T_6$ sequence as an oligonucleotide tag.

Functional group on ddNTP could be an amino (for example a propargylamino group routinely used for labeling nucleotides, Prober et. al., Science, 1987, 238, 336–341) which can react with an NHS ester group of bifunctional amidite, a thiol group reacting with maleimide, etc.

Another embodiment of the present invention provides a method of making an OTNTP on a solid support comprising following steps
 a) Synthesizing the desired oligonucleotide sequence on a solid support using routine automated DNA synthesis using fast deprotecting protecting groups on DNA bases,
 b) extending with modified nucleoside amidite carrying the amidite moiety at the base (as shown in example 1),
 c) deprotecting the 5'-OH group and phosphorylating the 5'-OH to give a triphosphate as described in the literature,
 d) cleaving the OTNTP from the support and deprotecting the said OTNTP.

Another embodiment of the present invention describes a method of making OTNTPs in solid/solution comprising following steps
 a) Synthesizing an oligonucleotide of desired sequence on a solid support and attaching a protected amino or thiol modified linker to the 5'-position of the oligonucleotide or having a phosphorothioate backbone on the 5'-end,
 b) Cleaving the oligo from the support and deprotecting the bases and the 5'-amino or thiol group,
 c) Reacting the functionalized oligo with a nucleoside triphosphate modified to contain a maleimide, epoxide or NHS ester on the base.

Another embodiment of current invention provides reactive bifunctional amidites of structures described below.

Some Examples of Bifunctional Linker Amidites

Where linker is linear or branched, saturated or unsaturated, acyclic, cyclic or aromatic compound and may contain one or more heteroatoms, such as, S, O, N or P R is a non-reactive polar or non-polar group R' is small alkyl or cyanoethyl and R" and R''' are independently selected from $C_1$–$C_6$ linear or branched alkyl or where R" and R''' form a 5–7 membered cyclic structure and may contain an additional heteroatom Another embodiment of current invention describes methods of making reactive bifunctional amidites. These amidites can be made by using a bifunctional linker alcohol and attaching a reactive group to the non-hydroxyl functional group. The hydroxy group is then reacted with tetraisopropylcyanoethylbis-phosphoramidite to give the reactive bifunctional amidite of the current invention. It should be noted that the non-amidite reactive functional group of this bifunctional amidite is stable enough to at least one cycle of coupling (tetrazole/acetonitrile) and oxidation (iodine/water/pyridine or 3H-1, 2-benzodithiol-3-one-1,1-dioxide (Beaucage reagent)) conditions used for oligonucleotide synthesis.

The invention is further described by reference to following examples. These examples are provided for illustrative purposes only and should not be construed as limiting the appended claims and the scope of this invention. The current invention should encompass any and all variations that become evident from the teachings provided herein.

EXAMPLES

Figure 3:
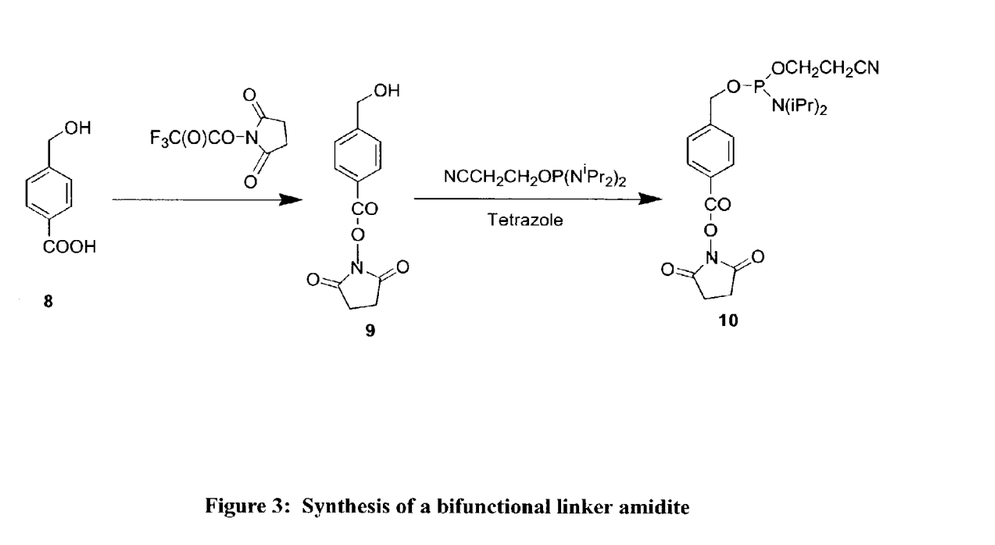
FIG. 3: Synthesis of a bifunctional linker amidite.
Figure 4:
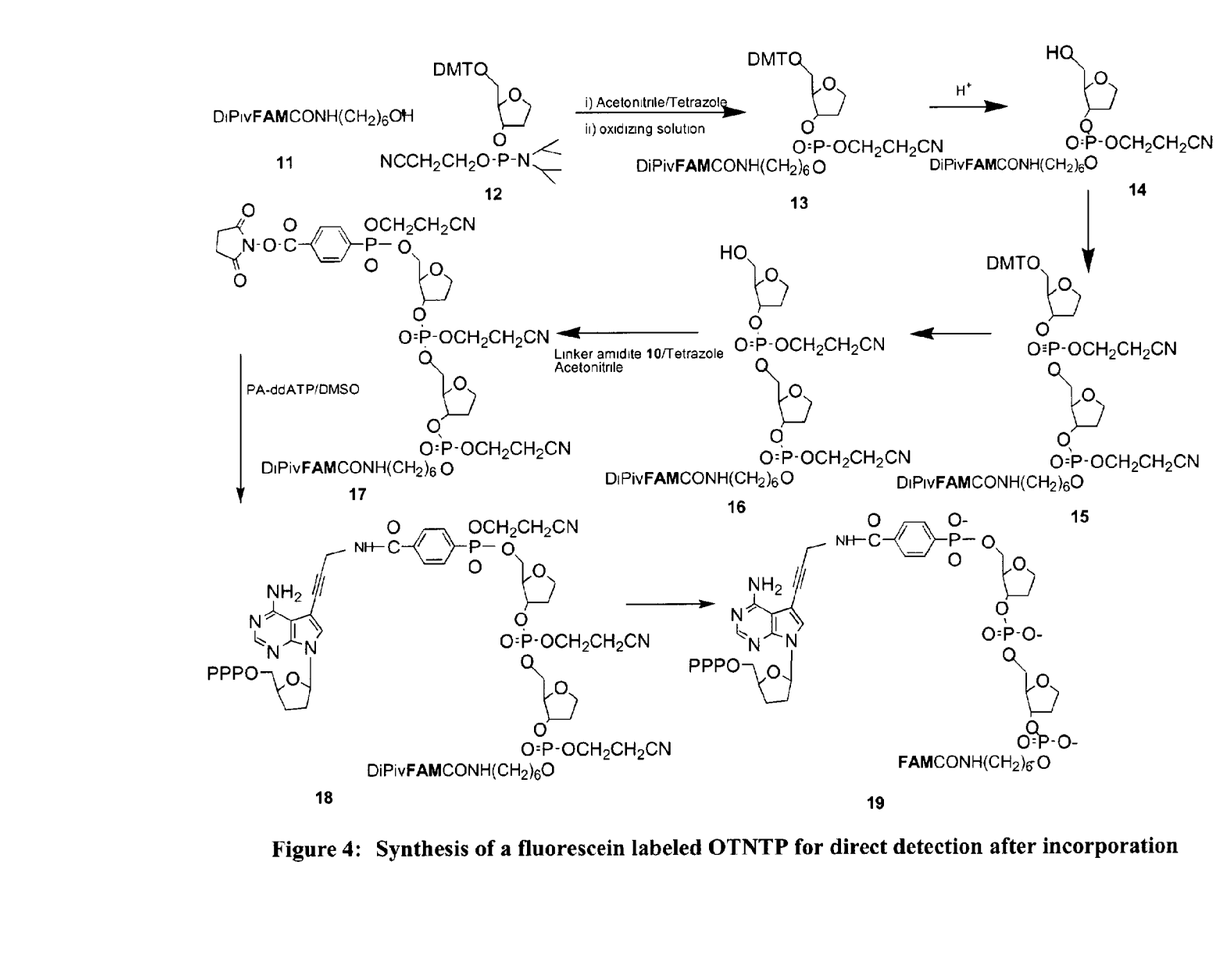
FIG. 4: Synthesis of a fluorescently labeled OTNTP for direct detection after incorporation.

The following examples are for illustration purposes only and should not be used in any way to limit the appended claims. Numbers that appear in bold below refer to the numbered compounds in FIGS. 2–4

Example 1

Figure 2:
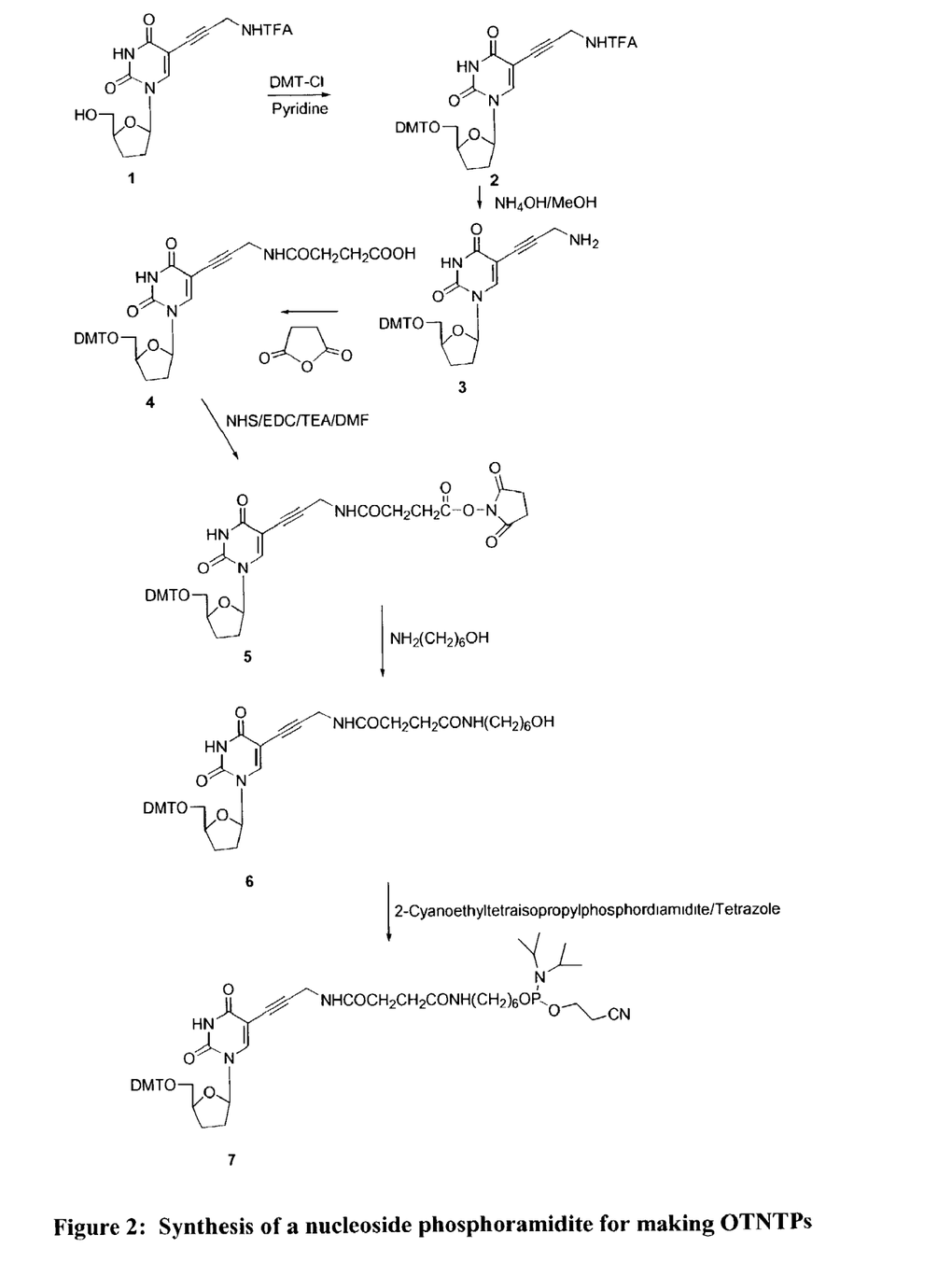
FIG. 2: Synthesis of a nucleoside amidite for making OTNTPs.

Synthesis of a Dideoxynucleoside-Linker Amidite, an Intermediate for Synthesis of Oligo Nucleotide Terminators (see FIG. 2).

5'-O-Dimethoxytrityl-5-propargylamino-2',3'-dideoxyuridine (3).

5-Propargytrifluoroacetamido 2',3'-dideoxyuridine (1, 1.0 g, 2.7 mmol) was dried by coevaporation with dry pyridine (2×10 ml), then it was dissolved in dry pyridine (10 ml) to which DMT-Cl (1.12 g, 3.3 mmol) was added. The reaction mixture was stirred at room temperature for 2.5 h, diluted with dichloromethane (75 ml) and washed with water (50 ml). Organic layer was dried (sodium sulfate), evaporated and the residue was coevaporated with toluene to remove traces of pyridine. The foam obtained was dissolved in methanol (20 ml) to which ammonium hydroxide (20 ml) was added. The mixture was stirred at room temperature for 3 h and evaporated to a small volume. The aqueous layer was extracted with dichloromethane. The organic layer was dried over sodium sulfate and evaporated. The residue was purified by silica gel column chromatography using 0–6% methanol-dichloromethane as the eluent. The appropriate fractions containing the product were collected and evaporated to give 1.15 g of 3.

$^1$H-NMR (CDCl$_3$): δ: 1.8–2.25 (m, 3 H), 2.45 (m, 1 H), 3.10 (br, 2H), 3.2 (dd, 1 H), 3.5 (dd, 1 H), 3.80 (s, 6 H), 4.25 (m, 1 H), 5.25 (s, 1 H), 6.05 (dd, 1 H), 6.80 (m, 4 H), 7.20–7.50 (m, 9H), 8.25 (s, 1 H), 11.60 (s, 1 H).

Synthesis of Amino Hexanol Derivative (6).

Compound 3 was dried by coevaporation with dry pyridine (10 ml). The dried substrate was dissolved in a mixture of dry dichloromethane (15 ml) and pyridine (5 ml) to which succinic anhydride (0.3 g, 3 mmol) was added. The reaction mixture was stirred at room temperature for 18 h and the reaction was quenched by the addition of water (1 ml). After 30 min diluted with dichloromethane (75 ml) and washed with water. Organic layer was dried (sodium sulfate) and evaporated.

The product obtained as above was dried by coevaporation with dry DMF (2×10 ml). The dried material was dissolved in DMF (8 ml) to which N-hydroxysuccinimide (0.28 g, 2.5 mmol), EDC (0.65 g, 3.4 mmol) and triethyl amine (0.47 ml, 3.4 mmol) were added and the reaction mixture was stirred at room temperature overnight. DMF was evaporated and the residue was partitioned between dichloromethane and water. Organic layer was dried and evaporated. The residue was dissolved in dichloromethane (10 ml) and 6-amino-1-hexanol (0.7 g, 6 mmol) was added. The reaction mixture was stirred at room temperature overnight, diluted with dichloromethane and washed with water. Aqueous layer was extracted with dichloromethane and the combined organic layer was dried over sodium sulfate, evaporated and the residue was purified by silica gel column chromatography using 0–5% methanol-dichloromethane as the eluent to give 0.75 g of 6.

$^1$H-NMR (DMSO-d6): δ 1.20–1.50 (m, 7 H), 1.80–2.20 (m 4 H), 2.30 (m, 3 H), 2.90–3.40 (m, 8 H), 3.70 (s, 6 H), 3.81 (d, 1 H), 4.20 (m, 1 H), 4.30 (t, 1 H), 5.90 (dd, 1 H), 6.90 (m, 4 H), 7.15–7.45 (m 9 H), 7,75 (t, 1 H), 7.82 (s, 1 H), 8.20 (t, 1 H).

Synthesis of Phosphoramidite 7.

Compound 6 was dried by coevaporation with a mixture of anhydrous acetonitrile and toluene. The residue was dissolved in dry acetonitrile (10 ml) to which 2-cyanoethyl tetraisopropylphosphorodiamidite (0.35 ml, 1.1 mmol) followed by tetrazole (77 mg, 1.1 mmol) were added under an argon atmosphere. The reaction mixture was stirred at room temperature for 45 min, diluted with dichloromethane (50 ml) and washed with cold sodium bicarbonate solution (20 ml). Organic layer was dried over sodium sulfate, evaporated and the residue was purified by column chromatography to give 0.62 g of 7.

$^{31}$P-NMR(CD$_3$CN): δ 147.94 ppm.

After coupling with an oligonucleotide on solid support and deprotection of the 5'-hydroxyl, it can be phosphorylated and converted to triphosphate on the solid support by previously described methods (R. K. Gaur et. al., Tet. Lett. 1992, 33, 3301–3304; A. V. Lebedev et. al., Nucleosides, Nucleotides & Nucleic Acids, 2001, 20, 1403 and references cited therein).

Example 2

Synthesis of a Reactive Bifunctional Amidite 4-(hydroxymethyl)-N-hydroxysuccinimidylbenzoate (9).

To a solution of 4-(hydroxymethyl) benzoic acid in dichloromethane (15 ml) and pyridine (3 ml) was added N-hydroxysuccinimidyltrifluoro acetate (3.48 g, 16.5 mmol) at 0° C. After the addition the reaction was continued at 0° C. for 5 min and then allowed to warm up by removing the ice bath. After 20 min the reaction mixture was diluted with dichloromethane (50 ml) and washed with water (3×50 ml). Organic layer was treated with methanol (10 ml). It was kept at room temperature for 20 min, dried over sodium sulfate and evaporated. The residue was coevaporated with toluene (10 ml) and dried under high vacuum to give 1.27 g of the product.

$^1$H-NMR(DMSO-$d_6$): δ 2.85 (s, 4 H), 4.60 (s, 2 H), 7.55 (d, 2 H), 8.05 (d, 2 H).

Phosphoramidite (10).

To a solution of 9 (0.75 g, 3 mmol) in dry acetonitrile (12 ml) was added tetrazole (0.23 g, 3.3 mmol) followed by 2-cyanoethyl tetraisopropylphosphorodiamidite (1.06 ml, 3.3 mmol) under an argon atmosphere. The reaction mixture was stirred at room temperature for 30 min, diluted with dichloromethane (100 ml) and washed with cold 0.5% sodium bicarbonate solution. Organic layer was dried (sodium sulfate) and evaporated. Finally it was purified by column chromatography utilizing 0.5% pyridine-dichloromethane as the eluent to give 1.27 g of the product.

$^1$H-NMR(CD$_3$CN): δ 1.20 (m, 12 H), 2.70 (t, 2 H), 2.85 (s, 4 H), 3.60–4.00 (2m, 4 H), 4.80 (m, 2 H), 7.60 (d, 2 H), 8.10 (d, 2 H); $^{31}$P-NMR(CD$_3$CN): δ 149.68 ppm Example 3

FAM-Aminohexanol-L-PAddUTP

To a solution of diPivFAM-aminohexanol 11 (50 mg) and bifunctional-linker-phosphoramidite 10 (35 mg) in dry acetonitrile (1 mL) was added tetrazole (22 mg) and the mixture was kept at room temperature for 5 min. The reaction mixture was diluted with dichloromethane and washed with cold 0.5% NaHCO$_3$ solution. The organic layer was dried over sodium sulfate and evaporated to dryness. The residue was dissolved in THF (5 mL) and oxidizing solution (0.1 N, 0.85 mL) was added dropwise. Two min after the addition the reaction mixture was diluted with dichloromethane and washed with 0.5% NaHSO$_3$ solution. Organic layer was dried and evaporated and the residue was coevaporated with toluene.

To about 20 mg of above obtained material in DMF (1 mL) was added a solution of PAddUTP (20 µmol) in DMF (1 mL). After stirring for 2 h, 8 mL of pH 9.5 buffer (carbonate/bicarbonate) and 4 mL of DMF was added and the reaction continued at room temperature for 20 h. The reaction mixture was treated with 10 mL of NH$_4$OH for 2 h and evaporated to near dryness. The residue was diluted with water and purified by ion exchange followed by reverse phase column chromatography.

Example 4

Synthesis of a Labeled OTNTP in Solution

Coupling of dipivaloylfluorescein-5-carbaxamidohexanol with DMT spacer phosphoramidite To a partial solution of fluorescein derivative (11, 0.26 g, 0.4 mmol) and tetrazole (84 mg, 1.2 mmol) in dry acetonitrile (1 ml) was added a solution of DMT spacer phosphoramidite (an abasic nucleoside amidite, 12, 0.25 g, 0.4 mmol) in acetonitrile (1 ml). The reaction mixture was stirred at room temperature for 20 min, diluted with dichloromethane and washed with cold 0.5% sodium bicarbonate solution. Organic layer was dried over anhydrous sodium sulfate and evaporated. The residue obtained was dissolved in acetonitrile (3 ml) and oxidizing solution (0.05 N iodine in water and pyridine, 8 ml) was added. After 30 min diluted with dichloromethane and washed with cold 0.5% sodium sulfite solution. The organic layer was dried over sodium sulfate and evaporated. The residue was purified by silica gel column chromatography to give 0.27 g of 13. $^{31}$P-NMR (CD$_3$CN): δ –1.25, –1.06 ppm.

Removal of DMT from Compound 13.

To a solution of 13 (0.27 g) in dichloromethane (3 ml) was added a solution of 2% DCA in dichloromethane (10 ml). The reaction mixture was stirred at room temperature for 20 min and the reaction was quenched by the addition of anhydrous ethanol (0.6 ml) and dry pyridine (0.9 ml). The reaction mixture was diluted with dichloromethane and washed with water. Organic layer was dried over sodium sulfate and evaporated. The residue was coevaporated with toluene to remove traces of pyridine and finally it was purified by silica gel column chromatography to yield 0.17 g of detritylated product 14.

Coupling of Second Spacer Amidite

In a similar manner as described for 13, compound 14 (0.17 g, 0.2 mmol) was coupled with spacer phosphoramidite (0.125 g, 0.2 mmol) in dry acetonitrile (3 ml) in the presence of tetrazole (42 mg, 0.6 mmol) which on oxidation with 0.05 N iodine solution gave the oxidized product 15 (0.18 g). Detritylation with DCA solution and purification by silica gel column chromatography gave 0.12 g of compound 16.

Coupling of Compound 16 with Bifunctional Amidite 10.

In a similar manner as described above 45 mg (0.04 mmol) of compound 17 and 18 mg (0.04 mmol) of bifunctional reagent were reacted in dry acetonitrile in the presence of tetrazole (8.4 mg, 0.12 mmol) and the coupled product on oxidation gave compound 17.

Conjugation of Propargylamino-ddATP with Compound 17.

To a solution of compound 17 (20 mg) in DMSO (1 ml) was added a solution of triphosphate in DMSO (1.5 ml) containing 2–3 drops of water. The reaction mixture was stirred at room temperature overnight and then treated with concentrated ammonium hydroxide (8 ml). After 4 h evaporated to a small volume, diluted with water and purified by ion exchange column chromatography using a gradient of 0.1 M TEAB +40% acetonitrile to 1.0 M TEAB +40% acetonitrile in one hour.

Example 5

Synthesis of FAM-T6-ddUTP

Commercially available FAM-CPG was used to synthesize a 3'-Fluorescein modified TTTTTT oligonucleotide.

Latter was further extended by reaction with bifunctional amidite 10. The NHS ester was then reacted with propargyl amino dideoxyuridine triphosphate to give the labeled OTNTP. After conjugation the oligo was unblocked from the solid support by treating with conc. ammonium hydroxide and purified by ion exchange followed by reverse phase column chromatography.

Example 6

Synthesis of FAM-LpLpLpLpLpLpLpT*-Linker-ddUTP's (Lp is deoxyribose-3'phosphate)

Figure 6:
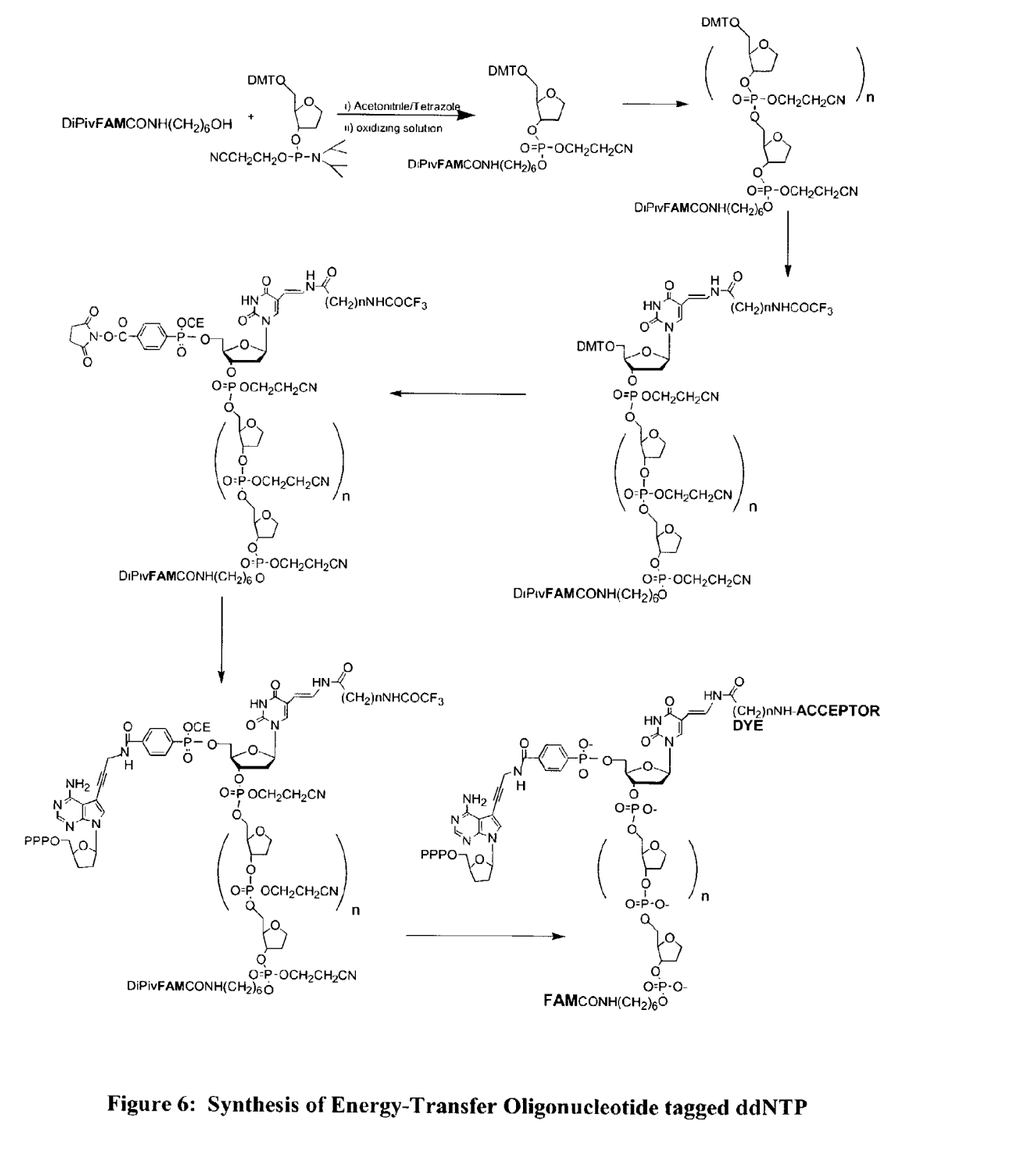
FIG. 6: Synthesis of Energy-Transfer oligonucleotide tagged dideoxynucleoside-5'-triphosphate (ddNTP).
Figure 7:
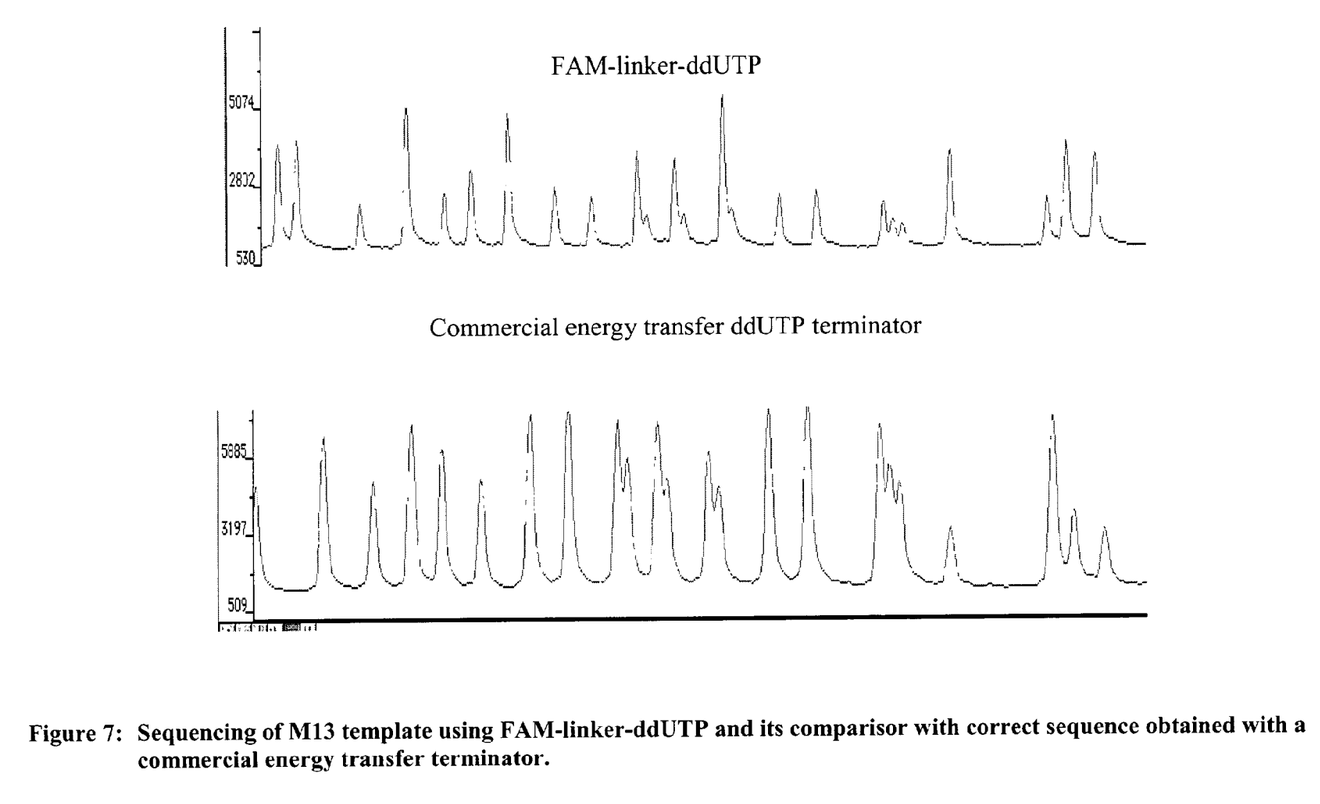
FIG. 7: Sequence data from sequencing of M13 (M13mp 18 (+)) template using FAM-linker-ddUTP (where FAM is carboxy-fluorescein).
Figure 8:
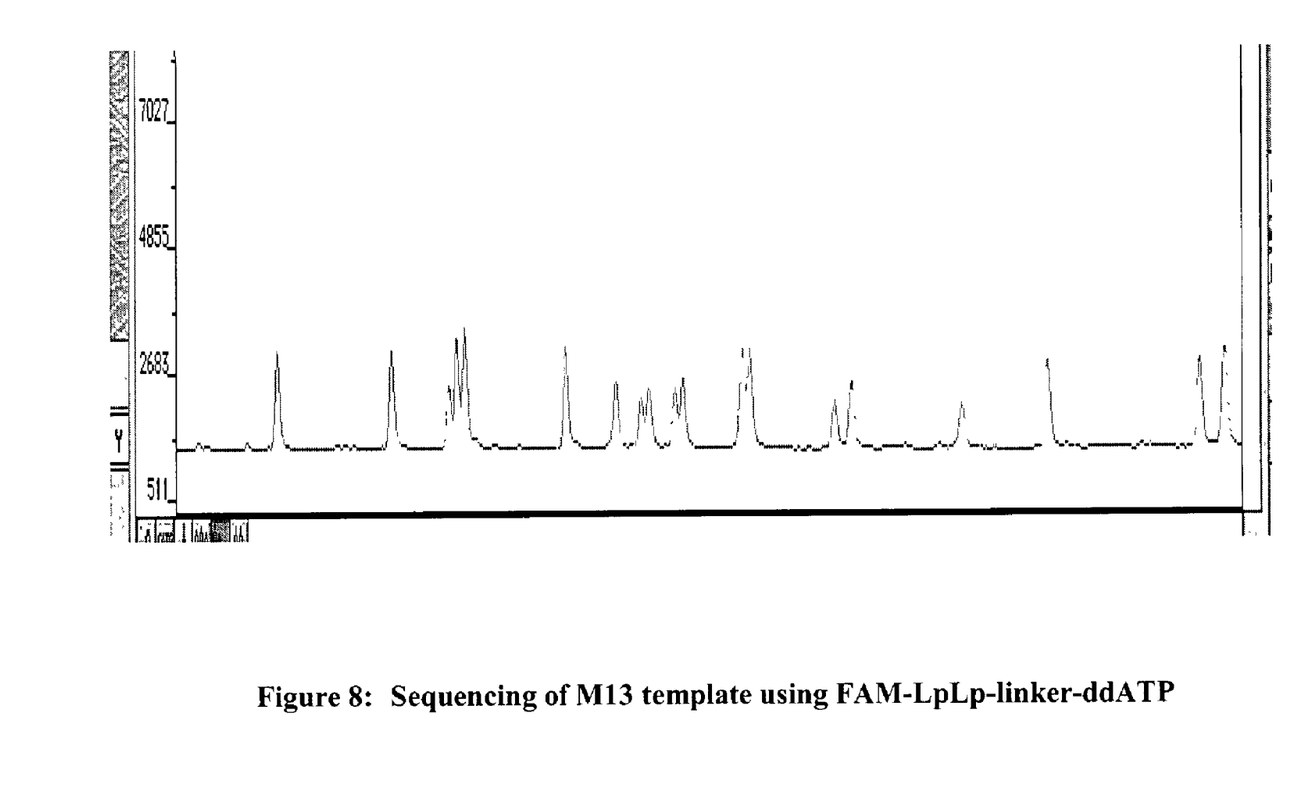
FIG. 8: Sequence data from sequencing of M13 template using compound 19 (see FIG. 4), FAM-LpLp-linker-ddATP (where Lp is deoxyribose-3'-phosphate).
Figure 9:
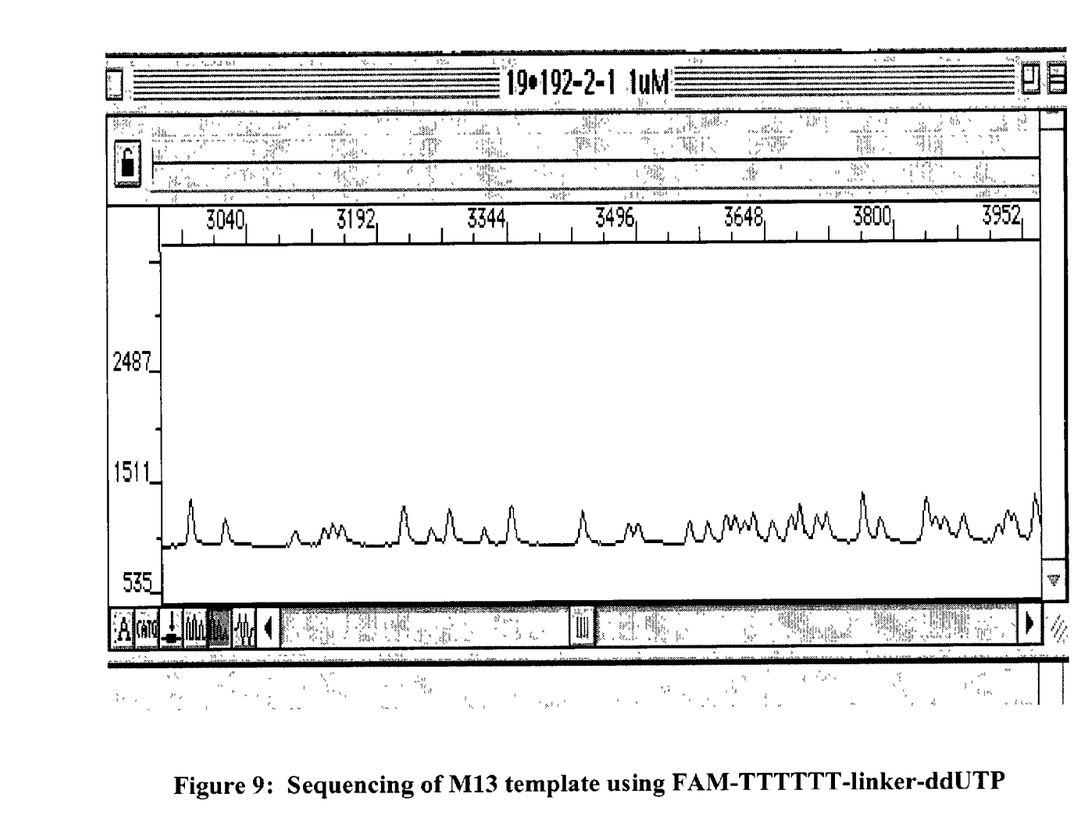
FIG. 9: Sequence data from sequencing of M13 template using FAM-(T)$_6$-ddUTP.
Figure 10:
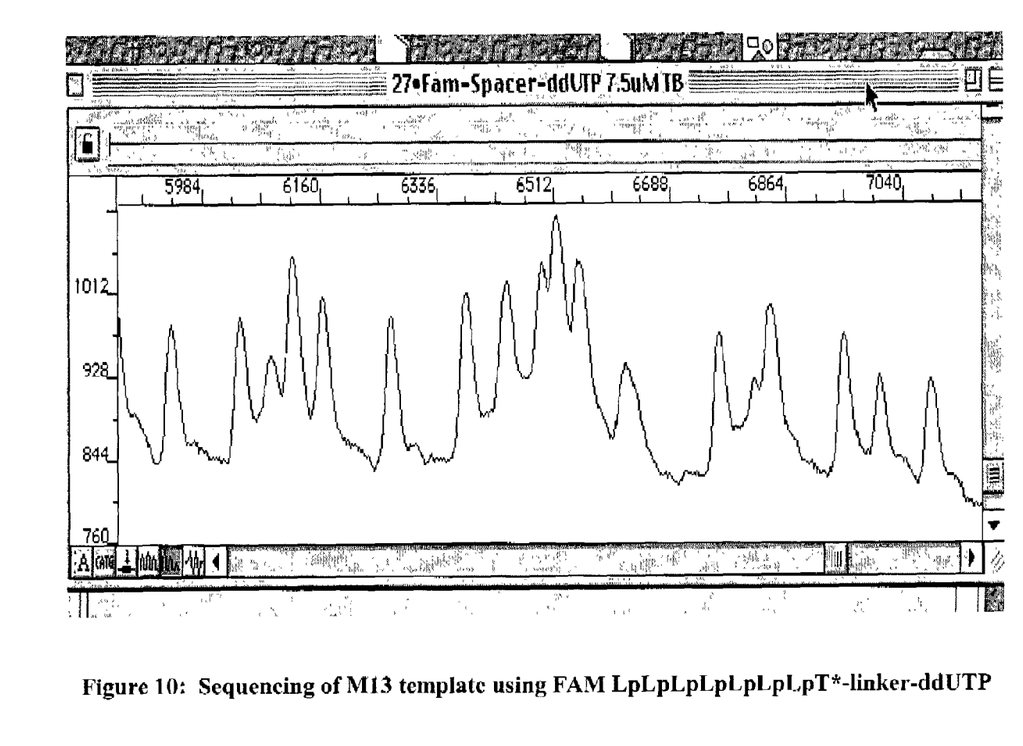
FIG. 10: Sequence data from sequencing of M13 template using FAM-LpLpLpLpLpLpLpT*-linker-ddUTP; Lp is as defined in examples.

Commercially available FAM support was extended on a DNA synthesizer using abasic sugar methylphosphoramidite. Oligo was further extended on the support using a modified T amidite called T*, which contains a protected amino functionalized group on the base which can be used to attach an acceptor dye. Oligo was further extended with amidite 10 and then reacted with an aminopropargyl ddUTP. After cleavage from support and deprotection, OTNTP was used for sequencing. To make an energy-transfer OTNTP, the amino group of the T* can be reacted with a functionalized acceptor dye as shown in FIG. 6.

Example 7

Sequencing of M13 Template using OTNTPs

Standard sequencing protocol for sequencing on ABI 377 Sequencer was used. Results are shown in FIGS. 7–10. In all cases, terminators were incorporated and gave accurate sequencing information.

A sequence of M13mp18 template DNA was generated using standard "-40" primer. The reaction mixture (20 μl) contained 200 μM each of dATP, dCTP, dTTP, and 1000 μM dITP, ~500 nM of OTNTP, 2 pmol -40 primer, 200 ng M13mp18 DNA. 20 units of Thermo Sequenase II or mutant Taq DNA polymerase (Amersham Biosciences), 0.0008 units Thermoplasma *acidophilum* inorganic pyrophosphatase, 50 mM Tris-HCl pH 8.5, 35 mM KCl and 5 mM MgCl$_2$.

The reaction mixture was incubated in a thermal cycler for 25 cycles of 95° C., 30 Sec; 60° C., 60 Sec. After cycling, the reaction products were precipitated with ethanol using standard procedures, washed, and resuspended in formamide loading buffer. The sample was loaded on an Applied Biosystems model 377 instrument and results were analyzed using standard software methods.

It would be clear using the above examples that other like nucleoside triphosphates, detectable labels (dye, energy-transfer dyes etc) may be attached to the normal or modified oligonucleotides or like structures and used for sequencing or other genetic analysis reactions.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The nucleotides, dyes, substituents, and target materials described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, those skilled in the art will readily recognize that the present OTNTPs can incorporate a variety of modified nucleoside phosphates (mono-, di-, tri- etc), monomers or oligomers, different dye moieties, linkers, attachment groups, and reactive groups, and can be attached to a variety of different target materials. Thus, such additional embodiments are within the scope of the present invention and the following claims.

In addition, where features or aspects of the invention are described in terms of Markush groups or other grouping of alternatives, those skilled in the art will recognize that the invention is also thereby described in terms of any individual member or subgroup of members of the Markush group or other group. Thus, additional embodiments are within the scope of the invention and within the following claims.

What is claimed is:

1. An OTNTP comprising the structure

Formula 1 wherein

R and R' independently represent H, OH, OCH$_3$, CH$_3$, N$_3$, SH, NCO, NCS, SCN NH$_2$, F, Cl or NR"R"', wherein R" and R"' independently represent H or a small chain C1–C5 alkyl;

X represents O, S, CH$_3$ or BH$_3$;

Base represents uracil, cytosine, thymine, adenine, guanine, hypoxanthine, 2-aminopurine, 2,6-diaminopurine, xanthene, deazaadenine, deazaguanine or an analog thereof;

Linker represents a linear or branched alkynyl, alkenyl, alkyl, alkylaryl, aryl, or arylalkyl containing one or more heteroatoms selected from the groups consisting of N, O, S and P, and is attached to the base;

N represents a ribose, deoxyribose, a natural or unnatural deoxyribonucleoside or a natural or unnatural ribonucleoside, wherein one or more of the N's is labeled with a fluorescent dye;

n represents an integer from 10 to 100; and wherein each N is linked to at least one other N by phosphodiester, phosphorothioate, alkyl phosphonate, or other linkages.

2. An OTNTP comprising the structure

Formula 1 wherein
R and R' independently represent H, OH, OCH$_3$, CH$_3$, N$_3$, SH, NCO, NCS, SCN NH$_2$, F, Cl or NR"R"',
wherein R" and R"' independently represent H or a small chain C1–C5 alkyl
X represents O, S, CH$_3$ or BH$_3$;
Base represents uracil, cytosine, thymine, adenine, guanine, hypoxanthine, 2-aminopurine, 2,6-diaminopurine, xanthene, deazaadenine, deazaguanine or an analog thereof;
Linker represents a linear or branched alkynyl, alkenyl, alkyl, alkylaryl, aryl, or arylalkyl containing one or more heteroatoms selected from the groups consisting of N, O, S and P, and is attached to the base;
N represents a ribose, deoxyribose, a natural or unnatural deoxyribonucleoside or a natural or unnatural ribonucleoside, wherein one of the N's is coupled to a donor dye and another N is coupled to an acceptor dye and there is energy transfer between the donor and acceptor when the donor dye is excited;
n represents an integer from 10 to 100; and
wherein each N is linked to at least one other N by phosphodiester, phosphorothioate, alkyl phosphonate, or other linkages.

3. An OTNTP comprising the structure

Formula 1 wherein
R and R"are both H;
X represents O, S, CH$_3$ or BH$_3$;
Base represents uracil, cytosine, thymine, adenine, guanine, hypoxanthine, 2-aminopurine, 2,6-diaminopurine, xanthene, deazaadenine, deazaguanine or an analog thereof;
Linker represents a linear or branched alkynyl, alkenyl, alkyl, alkylaryl, aryl, or arylalkyl containing one or more heteroatoms selected from the groups consisting of N, O, S and P, and is attached to the base;
N represents a ribose, deoxyribose, a natural or unnatural deoxyribonucleoside or a natural or unnatural ribonucleoside,
optionally containing a detectable moiety;
n represents an integer from 10 to 100; and
wherein each N is linked to at least one other N by phosphodiester, phosphorothioate, alkyl phosphonate, or other linkages.

* * * * *